United States Patent [19]

Orth et al.

[11] 4,040,936
[45] Aug. 9, 1977

[54] WET CHLORINE GAS GENERATOR FOR INSTRUMENT APPLICATIONS

[75] Inventors: Edward D. Orth, Boxford; John A. Roberts, Lynnfield, both of Mass.; Raymond J. D. Smith, Morrison, Ill.

[73] Assignee: General Electric Company, Schenectady, N.Y.

[21] Appl. No.: 711,024

[22] Filed: Aug. 2, 1976

[51] Int. Cl.² .......................... C25B 1/26; C25B 9/00
[52] U.S. Cl. .................................. 204/271; 204/262; 204/266; 204/274; 204/275; 204/278
[58] Field of Search ............... 204/271, 274, 275, 278, 204/94, 128, 129, 149, 195 R, 232, 236, 262, 266

[56] References Cited

U.S. PATENT DOCUMENTS

| | | | |
|---|---|---|---|
| 2,079,950 | 5/1937 | Negus | 204/271 X |
| 2,466,020 | 4/1949 | Goldberg | 204/271 X |
| 3,784,453 | 1/1974 | Dworkin et al. | 204/271 X |
| 3,812,026 | 5/1974 | Bertrand et al. | 204/278 X |

*Primary Examiner*—Arthur C. Prescott
*Attorney, Agent, or Firm*—Vale P. Myles

[57] ABSTRACT

A wet chlorine generator for providing precisely controlled rates of gas flow for instrumentation purposes, characterized by a safe and reliable gas source provided by precisely controllable electrolysis of a metal chloride electrolyte to form chlorine gas that is then passed through a flow regulating device into a gas conduit that guides the gas from the generator to associated instrumentation.

15 Claims, 4 Drawing Figures ant to the teaching of the present invention and illustrated with respect to a mounting frame.

WET CHLORINE GAS GENERATOR FOR INSTRUMENT APPLICATIONS

BACKGROUND OF THE INVENTION

It is desirable in many gas sensor instrument applications to have available a safe and reliable source of chlorine gas. Normally such instruments and their associated gas source are portable, thus they must be constructed to suitably withstand the mechanical shocks often encountered by portable instrumentation apparatus. It has been conventional practice to supply gas to these portable instruments by either mounting a replaceable gas flask in the instrument housing (or in associated holder means), or by providing the gas from a large fixed system and then diluting the chlorine gas with a suitable dilutant such as nitrogen by mixing it in a system that typically includes a series of pressure reducers, valves and flow meters that are operable to selectively meter the chlorine into a gas simple that is subsequently fed into an associated instrument at a desired flow rate. These kinds of conventional sources of chlorine gas for instrumentation purposes have been found to be generally effective for the purposes intended, but they involve several drawbacks that it would be desirable to avoid, if possible. For example, since a large supply of pressurized chlorine is necessarily available at all times in such conventional systems, there constantly exists a risk of escape of dangerous chlorine gas into the atmosphere. Such escape of gas can occur from a number of causes ranging from an inadvertent opening of the pressurized system to an accidentally caused leak or rupture developing in the system due to mishandling. In any case, the hazard is always present, even when the instrumentation system is not is use, since the system is, by its nature, constantly pressurized.

A further disadvantage of such relatively complex prior art systems is that the corrosive nature of chlorine gas makes it necessary to construct the component parts of the system from corrosion-resistant materials. The complexity of these systems and the associated costs of corrosion-resistant materials makes the overall expense of many such systems prohibitive. A further complicating factor often encountered in instrumentation applications for chlorine gas is that the gas must be moistened before it is suitable for given instrumentation uses; thus, it is often necessary to provide separate humidifying means to moisten the chlorine gas after it leaves its pressurized storage container, before it is introduced to the associated instrumentation. Again, the expense associated with providing the necessary corrosion-resistant components for these needed humidifier systems is undesirable and should be avoided if possible.

OBJECTS OF THE INVENTION

Accordingly, it is a primary object of the present invention to provide a wet chlorine gas generator that overcomes the above-mentioned disadvantages of prior art gas generators that are suitable for developing precisely controllable flows of chlorine gas for instrumentation purposes.

Another object of the invention is to provide a wet chlorine gas generator that safely provides and accurately controls gas flow at a rate that is suitably small for instrumentation applications.

Still another object of the invention is to provide a wet chlorine gas generator for portable instrumentation purposes that is characterized by being free from hazard caused by potential release of dangerous amounts of chlorine gas to the atmosphere when the generator is either in operation or in a stand-by condition.

Yet another object of the invention is to provide a wet chlorine gas generator that is inexpensive to construct, operate and maintain while being rugged and reliable in operation and precisely controllable insofar as its output of generated gas is concerned.

Additional objects and advantages of the invention will be apparent to those skilled in the art from the description of it that follows, taken in conjunction with the accompanying drawings.

SUMMARY OF THE INVENTION

In one preferred embodiment of the invention a wet chlorine gas generator for use with instruments requiring an accurately controlled rate of gas flow is provided, including a metal chloride electrolyte container in combination with electrodes and circuit means for effecting electrolysis of such an electrolyte in the container, and in further combination with precise flow regulating means for controlling the flow of chlorine gas from the generator into associated gas conduit means that are effective to transport gas to an indicating instrument. Liquid baffles and electric heaters are mounted in the generator to prevent condensate from forming at critical flow regulating portions thereof during operation of the generator.

DESCRIPTION OF THE PREFERRED EMBODIMENT

In the foregoing discussion of the background of the present invention it was noted that a number of different instrumentation applications require a precisely controlled supply of moistened chlorine gas. In order to facilitate the following description of the preferred embodiment of the invention and to further orient it relative to a typical instrumentation application, one such application will be briefly described before the detailed structure and function of a preferred embodiment is undertaken. Such an application of wetted chlorine gas for instrumentation purposes is involved in the use of a commercially available halogen gas sensor to detect the presence of acetones and certain other gases. In carrying out such an instrumentation application, it will be understood that a fairly precisely controlled flow of an atmospheric gas sample will be sniffed or otherwise drawn into a halogen sensor, such as the commercially available H-25 model, or "Ferret" sensor that is marketed by the Instrument Products Operation of General Electric Company located in Lynn, Mass. To make acetone or other given sampled gases detectable by such a sensor, it is necessary to introduce an accurately controlled flow of chlorine gas into the stream of sample gas before the mixture is passed through a heater-chlorinator and humidifier arrangement, which operates to halogenate the sample thereto suitably preparing it for introduction detection. This type of instrumentation application requires that a regulated flow of only a few parts per million of chlorine gas be mixed with the atmospheric gas sample and it is important that the rate of introduction of the chlorine gas be uniform and dependable so that appropriate continuous halogenation of the atmospheric sample will be achieved. As will be appreciated from the description that follows, the wet chlorine gas generator of the present invention is capable of supplying such a precisely regulated flow of chlorine gas in a reliable and completely safe manner.

Figure 1:
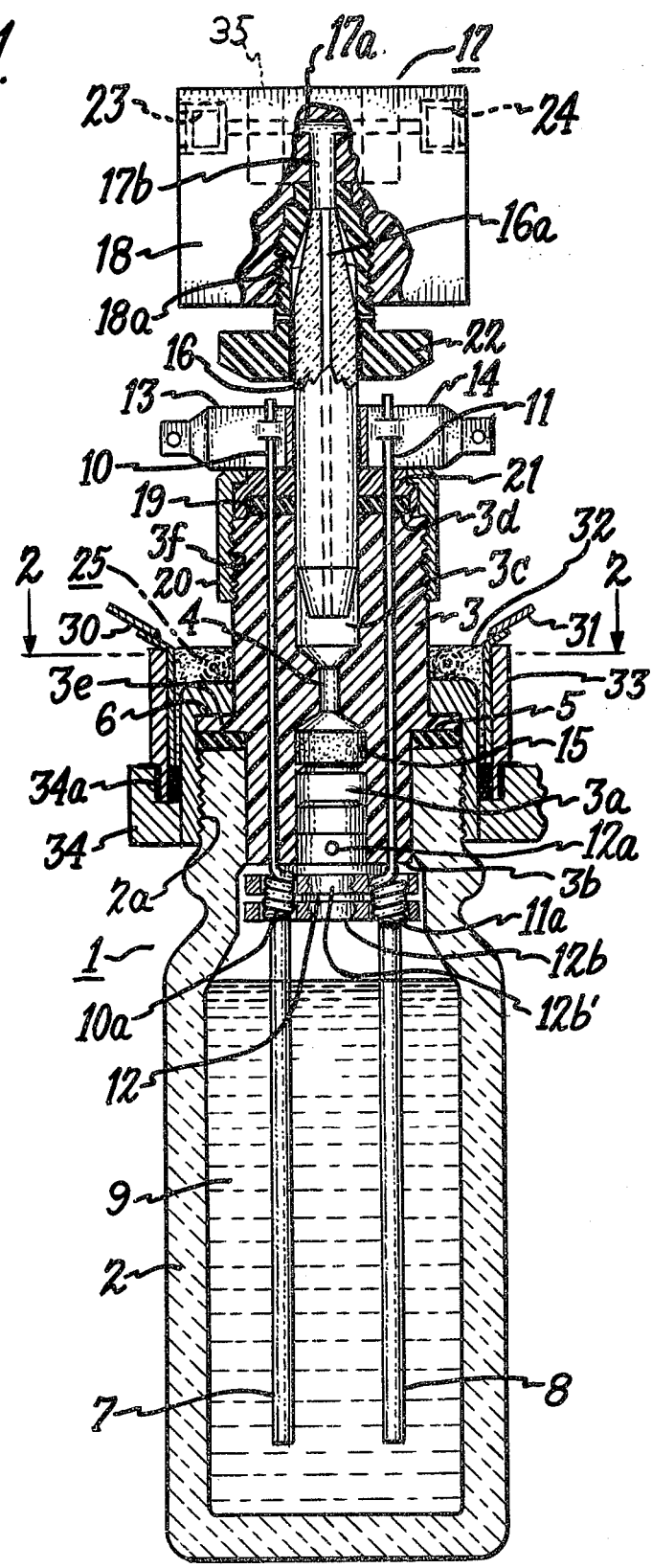
FIG. 1 is a front elevation view, partly in cross-section of a wet chlorine gas generator constructed pursuant to the teaching of the present invention and illustrated with respect to a mounting frame.

Referring now to FIG. 1 of the drawings the preferred embodiment of the wet chlorine gas generator 1 of the invention will be described. The generator 1 is formed of an open-ended impervious insulating container 2 that preferably is a glass bottle having a threaded neck 2a hereon. It is important in the manufacture of such a chlorine gas generator to use only component parts that are resistant to the very corrosive effect of sustained exposure to chlorine gas. Thus, while it will be recognized that other forms of containers may be used, such as containers fabricated with noble metals, the glass container 2 is preferred for its non-corrosive characteristics and commercial feasibility. A first corrosion-resistant plug 3 is positioned in the open end of the container 2 in order to substantially close the container. In this form of the invention, the plug 3 is molded Teflon which has been found to be highly resistant to the corrosive effect of chlorine gas and is readily available from the Dupont Company of Wilmington, DE. Obviously, other suitable corrosion-resistant materials may be used in alternative forms of the invention to manufacture plugs for similar gas generators made pursuant to the teaching of the invention. The plug 3 is provided with a first well 3a in the inner surface 3b thereof, a second well 3c in its outer surface 3d, and wall means defining a gas transmitting passageway 4 through it.

Seepage of gas between the open end of bottle 2 and the corrosion-resistant plug 3 is prevented by a first gas-type sealing means 5 that is disposed in sealing relationship between the plug and the container. Preferably, the sealing means 5 comprises a neoprene annular gasket that is compressed between an integral flange 3e on the plug and the top of the container 2 by screwing an open-centered threaded cap 6 onto the threads of the bottle neck 2a. Of course, other sealing and clamping means may be used in modifications of the invention but it is important to assure that the seal between the plug 3 and the bottle 2 remains absolutely gas tight (after extended exposure to chlorine gas under pressure) to prevent poisonous chlorine gas from escaping to the ambient atompshere.

A pair of graphite rod electrodes 7 and 8 are mounted in spaced, fixed relationship adjacent the inner end 3b of the plug 3 in a position such that they are substantially immersed in an electrolyte solution 9 that will be contained in the bottle 2 during its normal operation. Although relatively porous granular graphite rods have been found preferable for the electrodes 7 and 8 due to their effectiveness in forming relatively small bubbles of chlorine gas that are released in a fairly constant stream as electrolysis of the electrolyte 9 occurs, other types of electrode material such as corrosion-resistant platinum wire may be found suitable for some applications of the invention. Similarly, it has been found that a solution of nickel chloride is most preferably for the electrolyte 9 but other metal chloride salts such as copper chloride or sodium chloride may perform effectively in some applications of the invention. In this regard, however, it is desirable to note that a metal chloride electrolyte should be selected such that it is characterized by having a metal such as copper or nickel that will either be deposited on the electrodes or simply fall to the bottom of the container 2 as the electrolysis operation is performed.

A further advantage of the preferred nickel chloride electrolyte has been found to be that it can be conveniently and safely shipped in a dry powder state, then mixed in with water to form the desired electrolyte for the generator 1 when the equipment is to be placed in operation. This inherent safety of the nickel chloride solution is very important in the many intended instrumentation applications of it where safety is frequently a predominant consideration. Particularly in portable instrument application where the container 2 may be broken easily, or simply have electrolyte spilled from it during its periodic removal from a sealing relationship with the plug 3, the desirability of the inherently safe nature of the nickel chloride source of chlorine gas is obvious.

Various means may be used to mount the electrodes 7 and 8 in operating position within the container 2; however, in the preferred form of the invention a pair of corrosion-resistant wires 10 and 11, which are formed of platinum but may be made of other suitable materials, are mounted within the plug 3 to extend through it and beyond the inner end 3b and outer end 3d thereof, as shown in the drawing. Each of the platinum wires 10 and 11 is provided, respectively, with a coiled inner end 10a and 11a that is effective to receive and support therein one end of the respective electrodes 7 and 8. This unique mounting arrangement for releasably and resiliently holding the ends of electrodes 7 and 8 within the coils 10a and 11a of the electrical-grade platinum wires is particularly useful in simplifying the maintenance of the generator 1 of the invention. In this regard, when one of the electrodes, for example, the electrode 8, becomes heavily plated with nickel due to the electrolysis operation of the generator, it is a simple matter to remove the plug 3 from container 2 and then slide the electrode 8 from the resilient grip of the coil 11a of wire 11. After such removal a new electrode is simply inserted into the coil 11a so that operation of the generator can be renewed.

The electrodes 7 and 8 are further supported in their spaced relationship by a liquid baffle means 12 that is mounted at least partly within the first well 3a of the plug 3 to restrict electrolyte 9 from entering the wells 3a and 3c of the plug. As shown in the drawing, the liquid baffle means 12 comprises a second Teflon plug that includes wall means defining a gas receiving passageway 12a extending through it for guiding gas from the container 2 into the first well 3a. The second plug 12 is also formed to include a flange portion 12b that is arranged to prevent electrolyte from splashing into the passageway 12a in the second plug and thence into the well 3a. Actually, in the preferred embodiment the first flange 12b is supplemented by a second flange 12b' that is constructed by undercutting the lower portion of the plug 12 in the manner depicted. This arrangement has been found particularly desirable for enhancing the liquid baffling effect of the plug 12 and also for improving the supporting and spacing arrangement for the electrodes 7 and 8. Of course, as can be seen, the flanges 12b and 12b' are provided with suitable bored or otherwise formed apertures therethrough for receiving the coiled lower ends 10a and 11a of the platinum wires 10 and 11.

In order to conveniently connect a source of direct current electrical power to the platinum wires 10 and 11, their respective upper ends are clipped in conventional, commercially available terminals 13 and 14 that combine with the platinum wires 10 and 11 to form a suitable electrical circuit means (10, 11, 13 and 14) that is connected to the electrodes 7 and 8 to develop a voltage between them when the terminals 13 and 14 are connected to a suitable source of direct current electric power such as a battery (not shown).

In addition to the baffle means 12, a further baffle and gas diffusing means 15 is mounted in the first well 3a of the plug 3 to assure a desired degree of diffusion of gas bubbles flowing through the passageway 12a in the second plug 12 and thence through the passageway 4 in plug 3. Various corrosion-resistant, porous material may be used to form the disc 3, but in this embodiment of the invention a compressed disc of commercially available glass frit is used to make the diffusing means 15. It will be seen that in operation this disc of glass frit also serves to help prevent liquid electrolyte 9 from being aplashed into the passageway 4 and well 3c in plug 3.

A precisely controlled rate of gas flow is afforded from the generator 1, pursuant to a primary objective of the invention, by a pressure responsive gas flow regulating means 16 that is mounted in fixed relationship relative to the plug 3 and is arranged to receive gas flowing from the container 2 through the passageway 4 in plug 3. Although different types of pressure responsive flow regulating means may be employed in modified forms of the invention, in the embodiment being described, the pressure responsive flow regulating means 16 comprises a conventional, commercially available glass capillary tube that is formed with a flow regulating orifice 16a therein of a size that is effective to regulate the flow of chlorine gas from the container 2 into a gas conduit means 17 formed in a block 18 of corrosion-resistant electrical insulating material that will be described more fully below. It will be recognized that the pressure of gas applied to the capillary orifice 16a will partly determine the rate of flow of gas through it. In turn, it will be understood that gas pressure in the generator 1 will be partly determined by the current passed through the nickel chloride electrolyte solution 9 in the container 2. For many instrumentation applications such as the example given at the outset above for an acetone detector, it is desirable to make the capillary orifice 16a of a size that is effective to regulate the flow of gas from the container 2 into the conduit means 17 at a rate of about 2.5 × 10$^{-3}$ cubic centimeters of gas per second; responsive to a voltage being applied through the circuit means (10, 11, 13 and 14) to establish a current of approximately 20 milliamperes through the metal chloride electrolyte 9 in the container 2. Such a capillary tube is used in the preferred embodiment of the invention.

It is important to maintain the gas-tight integrity of the gas generator 1 at the junction of the capillary tube 16 and the upper end of plug 3, as well as at the junction of the capillary tube and the block 18. Toward this end, a second gas-tight sealing means 19 is disposed in sealing relationship between the plug 3 and the flow regulating means or capillary tube 16 to prevent gas flow therebetween. Various gasket materials may be used for this purpose but, again, a neoprene gasket is used to form the sealing means 19. The gasket 19 is compressed on the upper surface 3d of plug 3 by a threaded, hollow-centered cap 20 that engages suitable threads 3f molded or cut on the plug 3 and operates to clamp a gasket retaining annulus 21 onto the gasket 19. In addition to sealing the junction between the plug 3 and the capillary tube 16, the compressive operation of the hollow-centered cap 20 and the gasket retaining annulus 21 on the gasket 19 is effective to form a gas-tight seal around the wires 10 and 11 that extend through the plug 3 into the container 2. Thus, the second sealing means 19 that is mounted in sealing relationship around the circuit means (10 and 11) is effective to prevent chlorine gas from flowing out of the container 2 along the wires 10 and 11.

To assure a gas-tight seal between the conduit means 17 in block 18 and the capillary orifice 16a, a hollow threaded nut 22 is mounted in sealing relationship on and around the capillary tube 16 and is threaded into the threads 18a cut in insulating block 18 to form a seal between the flow regulating means 16 and the conduit means 17 in the block 18. Epoxy glue or other suitable sealing means are used to form the desired sealing relationship between the tube 16 and the nut 22 in this embodiment of the invention.

As mentioned at the outset, it is desirable in many instrumentation applications of the generator 1 of the invention to provide a precisely controlled mixing relationship of chlorine gas with a sample of atmospheric gas. To implement this objective, the conduit means provided in the insulating block 18 comprises a flow through passageway 17a for passing an atmospheric gas sample directly through the block from a suitable gas source, that may be connected to a conventional conduit terminal fitting 23, to a second or output terminal 24 that can be connected to a chlorinator-heater of the type described in the initial paragraph of the description of preferred embodiment of the invention, above. A spur gas passageway 17b is formed in the block 18 and is connected to receive gas from the orifice 16a of the flow regulating means 16 and transmit it into the flow-through passageway 17a to be intermixed with a gas sample therein. The block of material 18 may be formed of Teflon or other suitable corrosion-resistant, insulating material such as commercially available, moldable phenolic plastic.

Because of the need to continuously maintain a precisely controlled flow of chlorine gas from the generator 1, it is necessary to prevent the formation of condensate in either the conduit means 17 or the pressure responsive flow regulating means 16 of the generator. To accomplish that objective, a first heater means 25 is mounted adjacent the first plug 3 to heat it and thereby prevent moisture from condensing in the wells 3a, 3c or the passageway 4 thereof. A second heater means 35 is mounted adjacent the capillary tube 16 to heat it and prevent moisture from condensing therein.

Figure 2:
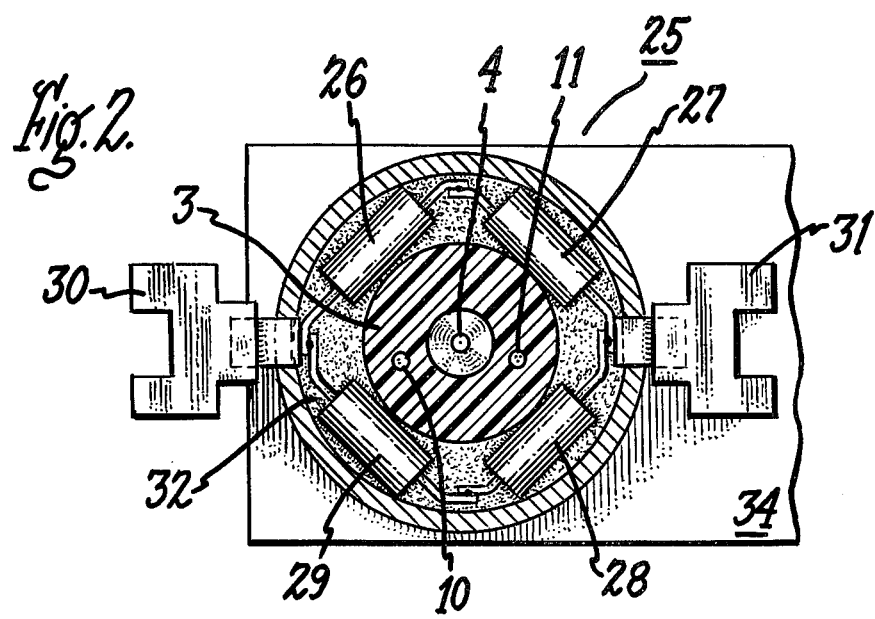
FIG. 2 is a top plan view along the plane 2—2 shown in FIG. 1 illustrating a first heater means used in the wet chlorine gas generator shown in FIG. 1.

The first heater means is best seen in FIG. 2 of the drawing. In its preferred form, the heater means 25 comprises four electrical resistors 26, 27, 28 and 29 that are electrically connected as shown in FIG. 2 between a first terminal 30 and a second terminal 31. The bottoms of these terminals and the resistors are potted in a suitable commercially available epoxy resin potting compound 32 that is positioned within a plastic sleeve 33 in sealing and thermally conductive relationship around the resistors 26-29. Preferably, the resistors 26-29 are each 2 watt resistors that are operable in combination, when connected to a suitable source of 110 volt A.C. power to develop a temperature of around 100° F in the potting compound 32 and the plug 3. Such a temperature level is effective to prevent the formation of condensate in the plug 3 which might otherwise undesirably partially or intermittently restrict the flow of gas to the capillary orifice 16 or through the passageway 4 in plug 3.

Before leaving the description of the first heating means, it should be noted that a variety of different assemblies may be used to support the container 2 and the associated heating means 25; however, in the preferred form of the invention these components are supported on an aluminum plate 34, which may form part of a larger instrumentation system, such as the above-mentioned modified H-25 model halogen gas detector system that is useful to detect acetone gases. As shown in the drawing, the sleeve 33 is glued with a suitable commercially available epoxy glue into a groove 34a and the glue is also effective to lock the open-centered cap 6 into position in the plate 34.

Figure 3:
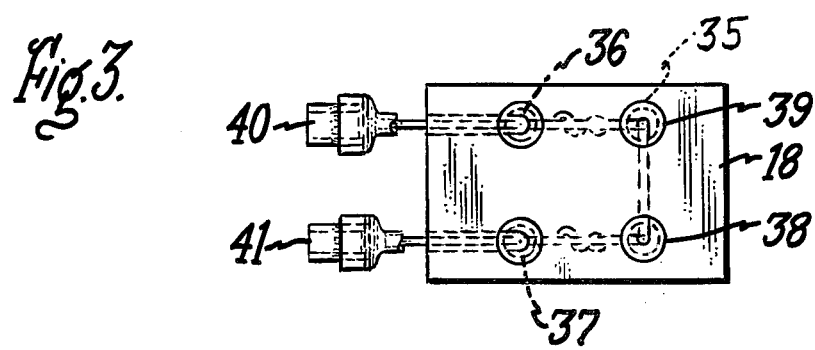
FIG. 3 is a top plan view, partly in phantom, illustrating the top surface of the gas generator shown in FIG. 1 and depicting in phantom a second heater means for the upper portion of the generator.
Figure 4:
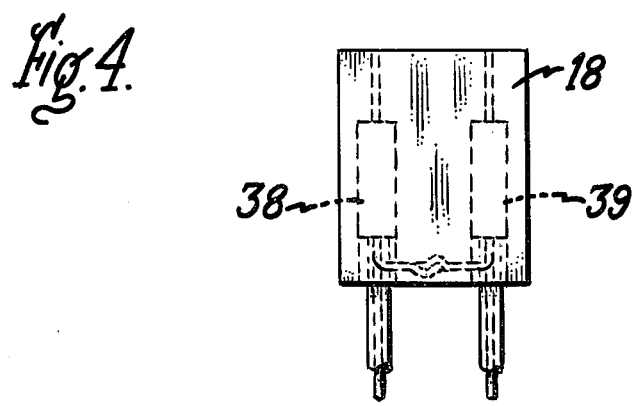
FIG. 4 is a side elevation view, partly in phantom, showing the right side of the top portion of the gas generator illustrated in FIGS. 1 and 3 and depicting in phantom two electrical resistors used in the second heater means partially illustrated in FIG. 3.

A second heater means 35 (best seen in FIGS. 3 and 4) is mounted adjacent the top of the capillary tube 16 and is encapsulated or housed within the block of insulating material 18. The second heater means 35 also comprises four electrical 2 watt resistors 36, 37, 38 and 39 that are electrically connected by the circuitry shown in phantom in FIGS. 3 and 4 between a first terminal 40 and a second terminal 41 in a conventional manner. Preferably, the terminals 40 and 41 are electrically connected respectively by circuit means (not shown) directly to the terminals 30 and 31 (see FIG. 2), so that when the terminals 30 and 31 are energized from a suitable 110 volt A.C. source both the first heater means 25 and the second heater means 35 will be energized. When such power is applied to the second heater means 35, it is effective to raise the temperature of the block 18 and the capillary tube 16 to a temperature of around 110° F. Thus, condensate will be prevented from forming in either the capillary orifice 16a or the conduit means 17 during the operation of the wet gas chlorine generator of the invention.

The operation of the generator 1 of the invention will be generally understood by those skilled in the art from the foregoing description of it; however, such operation may generally be summarized as follows: to place the generator 1 in operation, a metal chloride electrolyte, preferably a nickel chloride solution 9 is placed in the container 2 and the threaded neck 2a of the container 2 is screwed into the hollow-centered cap 6 to compress gasket 5 in sealing relationship with the flange 3e on the plug 3. A source 110 volt A.C. power is connected to terminals 30 and 31 to energize the first and second heater means 25 and 35. Then, a source of D.C. current is connected to the terminals 13 and 14 to cause a direct current of approximately 20 milliamperes to flow between the graphite rod electrodes 7 and 8. This current causes electrolysis of the electrolyte 9 resulting in nickel being deposited on one of the electrodes and a precisely controlled flow of small, relatively uniform-size chlorine gas bubbles rising from the granular electrodes, through the electrolyte 9 to the aperture 12a in the second plug 12. The wet gas then passes through the glass frit diffuser 15 and the passageway 4 in plug 3 and into the glass capillary tube 16.

As gas pressure builds up in the container 2, the evolved chlorine gas is forced through the capillary orifice 16a at a precisely controlled rate of approximately $2.5 \times 10^{-3}$ cubic centimeters per second and into the conduit means 17. Of course, in normal applications of the generator 1 of the invention, the conventional threaded terminals 23 and 24 will be connected to a gas sampling and sensing system that is effective to pass a regulated, relatively uniform flow of sample gas through the flow-through conduit 17a so that chlorine gas leaving the capillary orifice 16a will enter the spur conduit 17b and be intermixed with the sample gas and then discharged from the generator 1 into an associated mixing and sensor system such as the halogenating system described generally at the outset above.

Obviously a number of other applications of the generator 1 of the invention may be made, utilizing its safe and reliable operating characteristics that afford a precisely controlled flow rate of appropriately wetted chlorine gas only when the generator is activated. From the foregoing description of the invention it will be apparent to those skilled in the art that various alternative form and modified versions of it may be made without departing from the spirit of the invention; accordingly, the true scope of the invention is intended to be encompassed by the following claims.

What we claim as new and desire to secure by Letters Patent of the United States is:

1. A wet chlorine gas generator for instruments requiring an accurately controlled rate of gas flow, comprising an open-ended container for holding a metal chloride electrolyte solution therein, a first corrosion-resistant plug having wall means defining a gas transmitting passageway therethrough, said plug being positioned in the open end of said container to substantially close it but for said passageway, first gas-tight sealing means disposed in sealing relationship between the plug and the container to prevent gas flow therebetween, a pair of spaced electrodes mounted in fixed relationship adjacent the inner side of said plug, electrical circuit means connected to said electrodes to develop a voltage between them when connected to a source of direct current electric power, a pressure responsive gas flow regulating means mounted in fixed relationship relative to said plug and arranged to receive gas flowing from the container through the passageway in the plug, second gas-tight sealing means disposed in sealing relationship between the plug and said flow regulating means to prevent gas flowing out of the container along said circuit means, and gas conduit means connected to receive gas from said flow regulating means and guide the gas away from the container.

2. An invention as defined in claim 1 wherein said pressure responsive flow regulating means comprises a capillary tube having a flow regulating orifice therein of a size that is effective to regulate the flow of gas from said container to said gas conduit means at a rate of about $2.5 \times 10^{-3}$ cubic centimeters of gas per second responsive to a voltage being applied through the circuit means to establish a current of aproximately 20 milliamperes through a metal chloride electrolyte in the container.

3. An invention as defined in claim 1 wherein said plug is formed with a first well in the inner surface thereof and a second well in the outer surface thereof and with said gas transmitting passageway extending between said wells, said flow regulating means being a glass capillary tube having one end positioned within said second well, and including a liquid baffle means mounted at least partly within said first well to restrict electrolyte from entering said wells.

4. An invention as defined in claim 3 wherein said baffle means comprises a second plug including wall means defining a passageway therethrough for guiding gas from the container into said first well.

5. An invention as defined in claim 4 wherein said second plug includes a flange portion arranged to prevent electrolyte from splashing into said first well and passageway through the second plug, and wherein said circuit means comprises a pair of corrosion-resistant wires mounted to extend through the first plug and said flange, said corrosion-resistant wires each being provided with a coiled inner end for receiving and supporting therein, respectively, one of said spaced electrodes.

6. An invention as defined in claim 5 wherein said spaced electrodes comprise graphite rods, one end of each of said rods being releasably and resiliently held within the respective coiled inner ends of said corrosion-resistant wires, said wires being formed of electrical grade platinum.

7. An invention as defined in claim 5 including a diffusing means mounted in said first well in the first plug for diffusing gas bubbles flowing through the passageway in the second plug into the capillary tube.

8. An invention as defined in claim 1 including a first heater means mounted adjacent said first plug to heat it thereby to prevent moisture from condensing on the plug.

9. An invention as defined in claim 8 including a second heater means mounted adjacent said flow regulating means to heat it thereby to prevent moisture from condensing thereon.

10. An invention as defined in claim 9 including a block of corrosion-resistant electrical insulating material for housing said second heater means therein, said block of insulating material being formed with conduit means therethrough comprising said gas conduit means connected to receive gas from the flow regulating means.

11. An invention as defined in claim 10 including a threaded nut mounted in sealing relationship on and around said flow regulating means, said block being threaded onto said nut to form a gas-tight seal between the flow regulating means and the conduit means in said block.

12. An invention as defined in claim 19 including a sleeve positioned around said first heater means, and potting compound positioned within said sleeve in sealing and thermally conductive relationship around saaid first heating means.

13. An invention as defined in claim 11 including an electrolyte of nickel-chloride solution in said container, and wherein said spaced electrodes comprise graphite rods releasably mounted in relatively fixed positions adjacent said first plug.

14. An invention as defined in claim 13 wherein said first and second heater means comprise electrical resistance heaters and circuit means for supplying electrical power thereto.

15. An invention as defined in claim 11 wherein said gas conduit means through said block comprises a flow-through passageway for passing a gas sample through the block, and a spur passageway connected to receive gas from the flow regulating means and transmit it into said flow-through passageway to be intermixed with a gas sample therein.

* * * * *